(12) United States Patent
Silver

(10) Patent No.: US 7,094,785 B1
(45) Date of Patent: Aug. 22, 2006

(54) METHOD OF TREATING POLYCYTHEMIA VERA

(75) Inventor: Richard T. Silver, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 10/739,577

(22) Filed: Dec. 18, 2003

Related U.S. Application Data

(60) Provisional application No. 60/434,251, filed on Dec. 18, 2002.

(51) Int. Cl.
*A61K 31/497* (2006.01)
*A61P 35/00* (2006.01)

(52) U.S. Cl. .......................... 514/252.12; 514/252.14; 514/252.18; 514/256

(58) Field of Classification Search ........... 514/252.12, 514/252.14, 252.18, 256
See application file for complete search history.

(56) References Cited

U.S. PATENT DOCUMENTS

| 4,041,842 | A | 8/1977 | Stunkel | 91/448 |
|---|---|---|---|---|
| 4,140,122 | A | 2/1979 | Kuhl et al. | 128/260 |
| 4,383,529 | A | 5/1983 | Webster | 604/20 |
| 4,962,091 | A | 10/1990 | Eppstein et al. | 514/2 |
| 5,093,330 | A | 3/1992 | Caravatti et al. | 514/211 |
| 5,450,856 | A * | 9/1995 | Norris | 600/577 |
| 2003/0086924 | A1* | 5/2003 | Sliwkowski | 424/143.1 |
| 2004/0087546 | A1* | 5/2004 | Zeldis | 514/58 |

FOREIGN PATENT DOCUMENTS

| EP | 0564409 A1 | 10/1993 |
|---|---|---|
| WO | WO-9407529 A1 | 4/1994 |
| WO | WO-9835958 | 8/1998 |
| WO | WO-9903854 A1 | 1/1999 |
| WO | 03090750 A1 * | 11/2003 |

OTHER PUBLICATIONS

Remington: The Science and Practice of Pharmacy, Mack Publishing Co.,Nineteenth Edition, vol. 1, (1995), Chapter 48, "The Introduction of New Drugs", pp. 795-808.*

* cited by examiner

*Primary Examiner*—Christopher S. F. Low
*Assistant Examiner*—C. Delacroix-Muirheid
(74) *Attorney, Agent, or Firm*—Schwegman, Lundberg, Woessner & Kluth, P.A.

(57) ABSTRACT

The invention is directed to the use of imatinib mesylate for treating polycythemia vera. Imatinib mesylate is surprisingly effective at controlling the symptoms of polycythemia vera and reducing the need for phlebotomy.

6 Claims, 1 Drawing Sheet

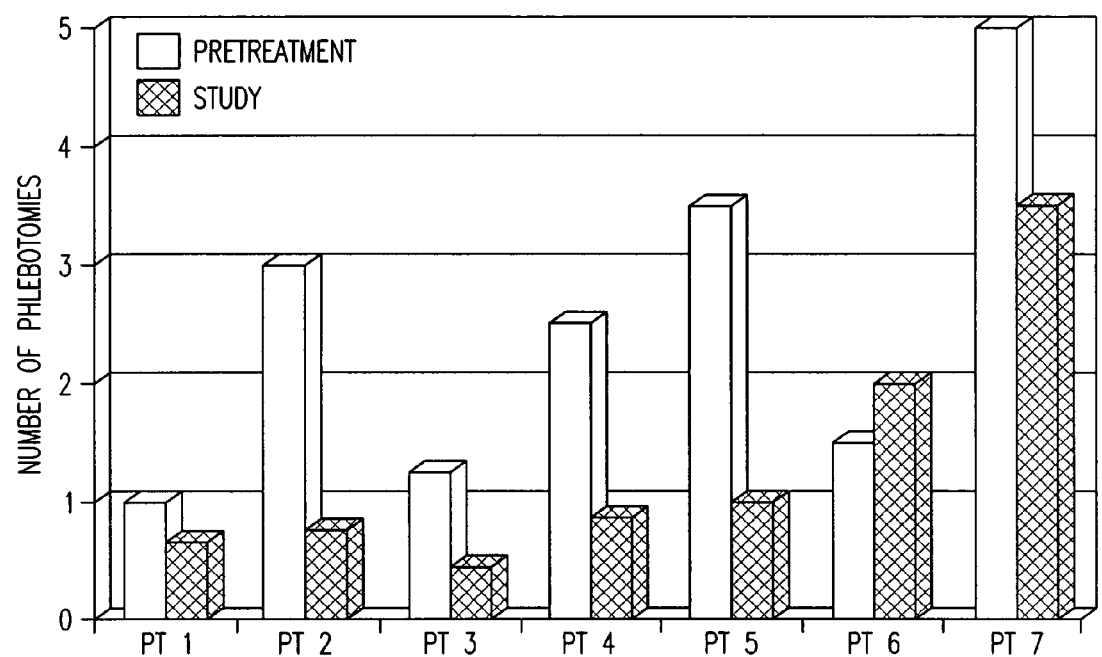

METHOD OF TREATING POLYCYTHEMIA VERA

This application claims priority to U.S. Provisional Application Ser. No. 60/434,251 filed Dec. 18, 2002.

FIELD OF THE INVENTION

The invention relates to the discovery that compounds related to N-{5-[4-(4-methyl-piperazino-methyl)-benzoylamido]-2-methylphenyl}-4-(3-pyridyl)-2-pyrimidine-amine, or pharmaceutically acceptable salts thereof, are useful for treating polycythemia vera.

BACKGROUND OF THE INVENTION

Polycythemia vera is a chronic myeloproliferative disorder. Typically, the disease is characterized by panmyelosis, splenomegaly and a predisposition to venous/arterial thrombosis, myelofibrosis and acute leukemia. Principal tests used in the diagnosis of polycythemia vera include determining the red cell volume, the serum erythropoietin level, the arterial blood gas, the leukocyte alkaline phosphatase score, the serum vitamin $B_{12}$ level, bone marrow biopsy, cytogenetics, and molecular markers. Further diagnostic means that can be employed are an abdominal computed tomography scan or a chest x-ray.

Phlebotomy alone or phlebotomy in combination with the administration of hydroxyurea or interferon currently constitute preferred approaches for treating polycythemia vera. However, newer, more effective drugs are needed to treat polycythemia vera in order to prevent progression of the illness to its inexorable end, severe fibrosis of the marrow ("marrow exhaustion") or less commonly, acute leukemia.

SUMMARY OF THE INVENTION

The present invention is directed to compositions and methods for treating polycythemia vera in warm-blooded animals, including humans, in which a therapeutically effective dose of a compound related to N-{5-[4-(4-methyl-piperazino-methyl)-benzoylamido]-2-methylphenyl}-4-(3-pyridyl)-2-pyrimidine-amine, or pharmaceutically acceptable salts thereof, is administered to a warm-blooded animal suspected of suffering from polycythemia vera. N-{5-[4-(4-methyl-piperazino-methyl)-benzoylamido]-2-methylphenyl}-4-(3-pyridyl)-2-pyrimidine-amine is commonly called imatinib mesylate. While imatinib mesylate has been used for treating patients with chronic myeloid leukemia, it is not effective for treating other myeloproliferative disorders such as essential thrombocythemia or myelofibrosis. Moreover, preliminary results indicate that imatinib mesylate is surprisingly effective in at least about 70% of patients with polycythemia vera.

DESCRIPTION OF THE FIGURE

FIG. 1 illustrates the phlebotomy (blood withdrawal) requirements per quarter (3 months) for each of the seven patients in the study before treatment (light bars) and after treatment (shaded bars) with imatinib mesylate.

DETAILED DESCRIPTION OF THE INVENTION

The present invention relates to a method of treating warm-blooded animals, including humans, in which a therapeutically effective dose of a of N-{5-[4-(4-methyl-piperazino-methyl)-benzoylamido]-2-methylphenyl}-4-(3-pyridyl)-2-pyrimidine-amine, or a pharmaceutically acceptable salt thereof, is administered to a warm-blooded animal suffering, or suspected of suffering, from polycythemia vera.

Compounds

The structure of N-{5-[4-(4-methyl-piperazino-methyl)-benzoylamido]-2-methylphenyl}-4-(3-pyridyl)-2-pyrimidine-amine that is employed is generally that of formula I:

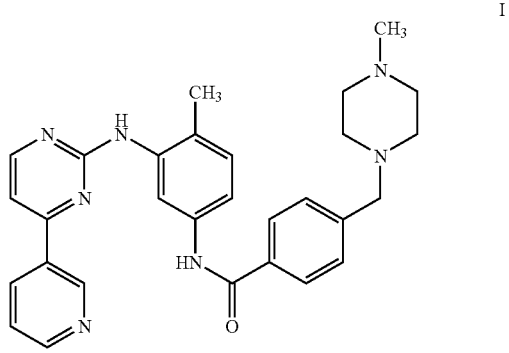

The mesylate salt of N-{5-[4-(4-methyl-piperazino-methyl)-benzoylamido]-2-methylphenyl}-4-(3-pyridyl)-2-pyrimidine-amine is commonly called imatinib mesylate and is marketed as Gleevec™.

Also according to the invention, related compounds can be used for treating polycythemia vera, including the compounds generically and specifically disclosed in the patent applications EP 0 564 409 A 1 and WO 99/03854, WO 98/35958, and U.S. Pat. No. 5,093,330, which are incorporated by reference herein. Moreover, the invention contemplates using the corresponding stereoisomers as well as the corresponding polymorphs, e.g. crystal modifications, which are disclosed therein in the treatment of polycythemia vera.

Hence, the present invention relates to a method of treating warm-blooded animals, including humans, in which a therapeutically effective dose of such compounds or pharmaceutically acceptable salts thereof are administered to a warm-blooded animal suffering from, or suspected of suffering from, polycythemia vera. The compounds of formula I and the pharmaceutically acceptable salts thereof are preferred. Special preference is given to the monomesylate salt of a compound of formula I.

Pharmaceutical compositions containing the compounds of the invention are prepared in any manner available to one of skill in the art, for example by means of conventional mixing, granulating, confectioning, dissolving or lyophilizing processes. The pharmaceutical compositions may be sterilized and/or may comprise excipients, for example preservatives, stabilizers, wetting agents and/or emulsifiers, solubilizers, salts for regulating the osmotic pressure and/or buffers. The pharmaceutical compositions can contain approximately from 1% to 100%, especially from approximately 1% to approximately 20%, active ingredient(s). Further details on formulating and administering the compounds of the invention are provided below.

Administration

The compounds of the invention, including their salts, are administered so as to achieve a reduction in at least one symptom associated with polycythemia vera, or a decrease in the frequency of phlebotomy required to control polycythemia vera. In some embodiments, the compounds of the invention can be administered after or concurrently with phlebotomy. Phlebotomy refers to the therapeutic withdrawal of blood. In other embodiments, polycythemia vera can be treated with the compounds of the invention without the need for phlebotomy.

The compounds of the invention are administered to a warm-blooded animal. Such a warm-blooded can be any mammal such as a dog, cat, pig, horse, goat, cow, steer or human. In some embodiments, the warm-blooded animal is a human.

To achieve the desired effect(s), the compound, a variant thereof or a combination thereof, may be administered as single or divided dosages, for example, of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results. The amount administered will vary depending on various factors including, but not limited to, the compound chosen, the severity of the disease, the weight, the physical condition, the health, the age of the mammal, whether prevention or treatment is to be achieved, and the like. Such factors can be readily determined by the clinician employing animal models or other test systems that are available in the art.

Administration of the therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of the compounds of the invention may be essentially continuous over a pre-selected period of time or may be in a series of spaced doses. Both local and systemic administration is contemplated, although systemic administration is generally preferred.

To prepare the composition, compounds are synthesized or otherwise obtained, purified as necessary or desired and then lyophilized and stabilized. The compound can then be adjusted to the appropriate concentration, and optionally combined with other agents. The absolute weight of a given compound included in a unit dose can vary widely. For example, a unit dose of about 1.0 to about 800 mg, or about 10 to about 400 mg, or about 100 to about 200 mg of at least one compound of the invention, or a plurality of related compounds can be administered.

Daily doses of the compounds of the invention can vary as well. Such daily doses can range, for example, from about 1.0 mg/day to about 2000 mg/day, from about 10 mg/day to about 1500 mg/day, from about 50 mg/day to about 1000 mg/day, from about 100 mg/day to about 1000 mg/day, from about 200 mg/day to 800 about mg/day, and from about 300 mg/day to about 800 mg/day.

Thus, one or more suitable unit dosage forms comprising the therapeutic compounds of the invention can be administered by a variety of routes including oral, parenteral (including subcutaneous, intravenous, intramuscular and intraperitoneal), rectal, dermal, transdermal, intrathoracic, intrapulmonary and intranasal (respiratory) routes. The therapeutic compounds may also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system.

When the therapeutic compounds of the invention are prepared for oral administration, they are generally combined with a pharmaceutically acceptable carrier, diluent or excipient to form a pharmaceutical formulation, or unit dosage form. For oral administration, the compounds may be present as a powder, a granular formulation, a solution, a suspension, an emulsion or in a natural or synthetic polymer or resin for ingestion of the active ingredients from a chewing gum. The active compounds may also be presented as a bolus, electuary or paste. Orally administered therapeutic compounds of the invention can also be formulated for sustained release, e.g., the compounds can be coated, microencapsulated, or otherwise placed within a sustained delivery device. The total active ingredients in such formulations comprise from 0.1 to 99.9% by weight of the formulation.

By "pharmaceutically acceptable" it is meant a carrier, diluent, excipient, and/or salt that is compatible with the other ingredients of the formulation, and not deleterious to the recipient thereof. The term "pharmaceutically acceptable salt" as used herein includes, but is not limited to acid addition salts, for example, salts formed by reaction with an inorganic acid, such as hydrochloric acid, sulfuric acid or a phosphoric acid, or with a suitable organic carboxylic or sulfonic acid, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or with an amino acid such as arginine or lysine, an aromatic carboxylic acid, such as benzoic acid, 2-phenoxy-benzoic acid, 2-acetoxy-benzoic acid, salicylic acid, 4-aminosalicylic acid, an aromatic-aliphatic carboxylic acid, such as mandelic acid or cinnamic acid, a heteroaromatic carboxylic acid, such as nicotinic acid or isonicotinic acid, an aliphatic sulfonic acid, such as methane-, ethane- or 2-hydroxyethane-sulfonic acid, or an aromatic sulfonic acid, for example benzene-, p-toluene- or naphthalene-2-sulfonic acid.

Pharmaceutical formulations containing the therapeutic compounds of the invention can be prepared by procedures known in the art using well-known and readily available ingredients. For example, the compound can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

For example, tablets or caplets containing the compounds of the invention can include buffering agents such as calcium carbonate, magnesium oxide and magnesium carbonate. Caplets and tablets can also include inactive ingredients such as cellulose, pre-gelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules containing at least one compound of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets containing one or more compounds of the invention are designed to resist disintegration in the stomach and dissolve in the more neutral to alkaline environment of the duodenum.

The therapeutic compounds of the invention can also be formulated as elixirs or solutions for convenient oral administration or as solutions appropriate for parenteral administration, for instance by intramuscular, subcutaneous, intraperitoneal or intravenous routes. The pharmaceutical formulations of the therapeutic compounds of the invention can also take the form of an aqueous or anhydrous solution or dispersion, or alternatively the form of an emulsion or suspension or salve.

Thus, the therapeutic compounds may be formulated for parenteral administration (e.g., by injection, for example, bolus injection or continuous infusion) and may be presented in unit dose form in ampoules, pre-filled syringes, small volume infusion containers or in multi-dose containers. As noted above, preservatives can be added to help maintain the shelve life of the dosage form. The active compounds and other ingredients may form suspensions, solutions, or emulsions in oily or aqueous vehicles, and may contain formulatory agents such as suspending, stabilizing and/or dispersing agents. Alternatively, the active compounds and other ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable carriers, vehicles and adjuvants that are well known in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol," polyglycols and polyethylene glycols, $C_1$–$C_4$ alkyl esters of short-chain acids, ethyl or isopropyl lactate, fatty acid triglycerides such as the products marketed under the name "Miglyol," isopropyl myristate, animal, mineral and vegetable oils and polysiloxanes.

It is possible to add, if desired by one of skill in the art, an adjuvant chosen from antioxidants, surfactants, other preservatives, film-forming, keratolytic or comedolytic agents, perfumes, flavorings and colorings. Antioxidants such as t-butylhydroquinone, butylated hydroxyanisole, butylated hydroxytoluene and α-tocopherol and its derivatives can be added.

Additionally, the compounds are well suited to formulation as sustained release dosage forms and the like. The formulations can be so constituted that they release the active compound, for example, in a particular part of the intestinal or respiratory tract, possibly over a period of time. Coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, catheters, peritoneal dialysis tubing, draining devices and the like.

The therapeutic agents may be formulated in wound dressings, coated bandages or other polymer coverings, ointments, creams, lotions, pastes, jellies, sprays, and aerosols. Thus, the therapeutic compounds of the invention can be delivered via patches or bandages for dermal administration. Alternatively, the compound can be formulated to be part of an adhesive polymer, such as polyacrylate or acrylate/vinyl acetate copolymer. For long-term applications it might be desirable to use microporous and/or breathable backing laminates, so hydration or maceration of the skin can be minimized. The backing layer can be any appropriate thickness that will provide the desired protective and support functions. A suitable thickness will generally be from about 10 to about 200 microns.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active compounds can also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1–85% by weight.

Drops, such as eye drops or nose drops, may be formulated with one or more of the therapeutic compounds in an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The therapeutic compound may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid carrier.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions pH 7.0–8.0.

The compounds of the invention can also be administered to the respiratory tract. Thus, the present invention also provides aerosol pharmaceutical formulations and dosage forms for use in the methods of the invention. In general, such dosage forms comprise an amount of at least one of the agents of the invention effective to treat or prevent the clinical symptoms of polycythemia vera. Any statistically significant attenuation of one or more symptoms of polycythemia vera that has been treated pursuant to the method of the present invention is considered to be a treatment of polycythemia vera and is within the scope of the invention.

Furthermore, the active ingredients may also be used in combination with other therapeutic agents, for example, pain relievers, anti-inflammatory agents, anti-platelet agents, blood thinning agents and the like can be included in the therapeutic compositions of the invention.

The present invention further pertains to a packaged pharmaceutical composition for controlling polycythemia vera such as a kit or other container. The kit or container holds a therapeutically effective amount of a pharmaceutical composition for controlling polycythemia vera and instructions for using the pharmaceutical composition for control of polycythemia vera. The pharmaceutical composition includes at least one compound of the present invention, in a therapeutically effective amount such that polycythemia vera is controlled. The kit or commercial package can also include a means for performing phlebotomy. Such a means for performing phlebotomy can include a needle, a syringe, a catheter or a blood collection bag.

The invention is further illustrated by the following non-limiting Examples.

EXAMPLE 1

Imatinib Mesylate Effectively Treats Polycythemia Vera

Seven patients with polycythemia vera were studied to determine whether phlebotomy (blood withdrawal) requirements could be reduced and whether hematocrit levels could be normalized by treatment with imatinib mesylate. The effect of imatinib mesylate on splenomegaly (if present) and on side effects and the general quality of life of the patients were also noted.

Polycythemia vera was diagnosed by the diagnostic criteria shown in Table 1. Any three of the six criteria shown in Table 1 were required for a positive diagnosis.

TABLE 1

| PV diagnostic criteria |
| --- |
| Red cell mass > 25% above normal predicted value |
| Exception: men with hct > 60% or women with hct > 56% |
| Exclude secondary erythrocytosis |
| Any three of the following: |
| Clinically palpable spleen |
| Bone marrow consistent with PV |
| Clonality markers (cytogenetic abnormalities) |
| Platelet count > 600000/µl |
| WBC > 12000/µl |
| Serum epo level < 25 mU/ml |

Hence, patients were screened for an increased red cell mass, defined as an increase >25% above the normal predicted value, except for men with a hematocrit of >60% or women with a hematocrit >56%. $^{131}$I plasma volume was also determined. In all cases, bone marrow aspiration smears stained for iron disclosed absent iron stores. Patients were also screened for chronic myeloid leukemia by cytogenetic studies; in all cases patients used in the study did not reveal the Philadelphia chromosome indicative of chronic myeloid leukemia. Patients employed in the study were either newly diagnosed, interferon refractory, resistant or intolerant, or their disease was not controlled by hydroxyurea.

The demographics of the seven patients studied to date are shown in Table 2. The three men and four women were relatively young, stressing the importance in carefully selecting therapy for individuals under the age of 50 years. Prior treatments in addition to phlebotomy are shown in Table 2.

TABLE 2

| Demographics | |
| --- | --- |
| Sex | |
| Male: | 3 |
| Female: | 4 |
| Age (years) | |
| Median: | 53 y |
| Ages: | (29, 32, 41, 53, 69, 74, 76) |
| Prior treatments(s) | |
| Hydroxyurea: | 1 |
| Interferon: | 1 |
| Anagrelide: | 2 |
| Disease duration | |
| Median: | 12 months |
| Range: | 1.2–18 months |

Treatment was started at a dose of 400 mg daily. Dose escalation was permitted to a maximum of 800 mg daily for persistent phlebotomy requirements, thrombocytosis, or spenomegaly.

Treatment duration has only lasted approximately 6 months to date. Nevertheless, if we examine the change of phlebotomy requirements for 3 month periods before and during imatinib therapy, there is change in six of seven patients (FIG. 1). Because not all patients were seen by the inventors initially, and because they may not have been phlebotomized with the same vigor with which the inventors do, these differences may even have been greater.

The months on trial and the phlebotomy requirements at baseline and during treatment are provided in Table 3. The months free of phlebotomy are shown in the last column. The second patient had grade 3 dermatitis and was removed from study 1.6 months after beginning imatinib mesylate; this patient has since required two phlebotomies. All patients had an elevated platelet count before or during imatinib mesylate and four have returned to below 600,000/µl while three remain elevated.

TABLE 3

| Change in phlebotomy requirements | | | |
| --- | --- | --- | --- |
| Phlebotomy requirement | | Months on | Phlebotomy Free |
| Baseline | During Rx | Trial | Months |
| 1 | 1 | 9.1 | 8.6 |
| 6 | 1 | 3.7 | 1.6* |
| 5 | 1 | 7.5 | 6.8 |
| 5 | 2 | 7.2 | 4.5 |
| 7 | 2 | 6.8 | 3.2 |

TABLE 3-continued

Change in phlebotomy requirements

| Phlebotomy requirement | | Months on Trial | Phlebotomy Free Months |
|---|---|---|---|
| Baseline | During Rx | | |
| 12 | 4 | 6.0 | 1.1 |
| 5 | 7 | 6.2 | 0.7 |

*Patient off-study: Two phlebotomies post-imatinib.

Change in spleen size occurred in two patients who had an enlarged spleen prior to imatinib. In one, it reduced in size by 75%, and in the second, a patient with a much smaller spleen, it became nonpalable.

Six of seven patients required an increase in imatinib dose because of persistent thrombocytosis, splenomegaly, or phlebotomy requirements to date. In five, the dose was more than 500 mg daily. Imatinib mesylate was remarkably well tolerated except for one patient who developed grade 3 dermatitis for whom it had to be discontinued.

Therefore, imatinib mesylate is effective in polycythemia vera in reducing phlebotomy requirements, in lowering abnormal platelet counts, and reducing spleen size. Continued investigation is warranted to determine long-term response, optimum dose, duration, and side effects.

EXAMPLE 2

Further Studies Illustrate the Effectiveness of Imatinib Mesylate for Treatment of Polycythemia Vera Another clinical study was conducted using procedures like those described in Example 1. Twenty patients suspected of having polycythemia vera (as determined by the criteria in Table 1) were enrolled in this study. After treatment with imatinib mesylate ten patients had a complete remission of symptoms and four patients had a partial remission. It was too early to evaluate four other patients, one patient appeared to not respond to treatment and the final patient was later diagnosed as not having polycythemia vera.

Hence, at least about 70% of patients treated with imatinib mesylate in this study responded positively. Accordingly, administration of effective dosages of imatinib mesylate appears to be a highly effective treatment for polycythemia vera.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method of treating polycythemia vera in a warm-blooded animal in need thereof comprising administering to the warm-blooded animal a therapeutically effective amount of N-{5-[4-(4-methyl-piperazino-methyl)-benzoylamido]-2-methylphenyl}-4-(3-pyridyl)-2-pyrimidine-amine or a pharmaceutically acceptable salt thereof to thereby reduce at least one symptom of polycythemia vera.

2. The method of claim 1, wherein the therapeutically effective amount comprises about 100 mg/day to about 2000 mg/day.

3. The method of claim 1, wherein the therapeutically effective amount comprises about 400 mg/day to about 800 mg/day.

4. The method of claim 1, wherein the warm-blooded animal is a human.

5. The method of claim 1, wherein the pharmaceutically acceptable salt is a mesylate salt.

6. The method of claim 1, wherein the pharmaceutically acceptable salt is a monomesylate salt.

* * * * *